US005146912A

United States Patent [19]

Eizenhoefer

[11] Patent Number: 5,146,912

[45] Date of Patent: Sep. 15, 1992

[54] VARIABLE ENERGY SHOCK WAVE PRODUCTION

[75] Inventor: Harald Eizenhoefer, Johannesberg, Fed. Rep. of Germany

[73] Assignee: Dornier Medizin Technik, Fed. Rep. of Germany

[21] Appl. No.: 598,225

[22] Filed: Oct. 16, 1990

Related U.S. Application Data

[63] Continuation-in-part of Ser. No. 311,461, Feb. 16, 1989, abandoned.

[30] Foreign Application Priority Data

Feb. 18, 1988 [DE] Fed. Rep. of Germany ....... 3804993

[51] Int. Cl.$^5$ ............................................ A61B 17/22
[52] U.S. Cl. ................................ 128/24 EL; 367/147
[58] Field of Search ................... 128/24 EL; 367/147; 313/124, 136

[56] References Cited

U.S. PATENT DOCUMENTS 4,809,682 3/1989 Forssmann et al. ........... 128/24 EL

FOREIGN PATENT DOCUMENTS 2635635 9/1978 Fed. Rep. of Germany ... 128/24 EL

OTHER PUBLICATIONS

"ESWL-New Aspects in the Treatment of the Disease", Chauss, C. H., et al., Karger, A. G., Germany, 1982, pp. 10–11.

*Primary Examiner*—Kyle L. Howell
*Assistant Examiner*—Scott R. Akers
*Attorney, Agent, or Firm*—R. H. Siegemund

[57] ABSTRACT

An arrangement for the comminution of concrements of various kinds in the body of living being, uses an underwater or submerged arc gap with spark discharge, and an electrical energizing circuitry for that arc gap, a plurality of electrode assemblies from which one is selected to be used in the equipment is connected to the energizing circuit; the electrode assemblies are basically similarly configured and each has an ohmic resistor which is connected directly in series with one of the electrodes, the resistance value for the resistors in the electrode assemblies of the plurality are different, and in each instance much lower than the resistance of the unignited gap, but of comparable magnitude with the resistance of a fully developed plasma channel in the gap following ignition by the energizing circuit.

4 Claims, 1 Drawing Sheet

VARIABLE ENERGY SHOCK WAVE PRODUCTION

This application is a continuation-in pat of application Ser. No. 311,461, filed Feb. 16, 1989 and now abandoned.

BACKGROUND OF THE INVENTION

The present invention relates to medical shock wave treatment and here particularly to the contactless comminution of concrements in the body of a living being under utilization of a submerged arc discharge serving as a shock wave generator, there being an appropriate switching and operating structure for the generator.

Concerning the technology generally and the comminution of concrements in particular, reference is made to German patent 23 51 247 corresponding to U.S. Pat. No. 3,942,531, and other patents of common assignee. Typical arc discharge devices and units in conjunction with which the invention can be practiced with advantage are shown e.g. in U.S. Pat. Nos. 4,608,983 and 4,809,682. Positioning electrode exchange units are shown e.g. in U.S. Pat. No. 4,040,050. Moreover, specific reference is made to a brochure by Ch. Chaussy ed., "Extracorporeal Shock wave Lithotripsy", giving an extensive background treatment on the subject mater including the comminution process itself and the generation of shock waves in particular.

Broadly speaking therapeutic shock wave generation uses a spark gap produced by a discharge between electrodes the discharge through the gap between the electrodes results from the discharge of an electric capacitor. That capacitor is discharged in certain instants. The capacitor is recharged thereafter, requiring a certain period of time for such a restoration but the discharge itself is a phenomenon of very short duration. Since the electrodes are submerged, on discharge a shock wave is produced in the water. A rotational ellipsoid partially encloses the spark gap which is situated in one of the two focal points of that rotational ellipsoid. As shock waves are produced by the gap in that one focal point they are reflected by the rotational ellipsoid and are refocused in the second focal point for comminuting concrement thereat.

The acoustic energy that can be concentrated in the body of the person, depends on the efficiency of coupling the waves to the body. From a primary point of view the discharge depends on the amount of electrical energy that is fed into the discharge device. Specific relevant parameters include the voltage and the capacitance of the capacitor. Generally speaking, one needs some form of control over the intensity and energy of the shock wave and, therefore, it is desirable to provide for a certain, possibly even large variability of the shock wave energy. Depending on the medical specifics; a rather broad energy spectrum is quite desirable.

Gall stones require usually a higher energy level for their comminution than is necessary for the destruction of kidney stones. It is obvious that the same equipment should be suited for both kinds of treatment, comminution of kidney stones, as well as comminution of gall stones. Consequently this requirement of multiple use carries with it the requirement of making available a fairly wide range of energy.

Shock wave energies can easily be varied through variation of the voltage that is applied to the capacitor for charging it. Variation of that voltage controls the amount of charge on the capacitor. However, the ignition properties of the submerged arc limit the range of variability of the voltage that can be accommodated. Another factor to be considered is that multiple use of the same electrodes entails certain burn-off which inherently increases the voltage minimum for obtaining any ignition at all. The required energy thus increases with the frequency of use and burn-off of the electrodes. Hence, the discharge and shock producing energy cannot be reduced to any level below that minimal level needed for the ignition process. Another way of controlling the shock wave energy, of course, is the variation of the capacitance. While such an approach is feasible in principle it requires high voltage and/or high current switches which are mechanically bulky and expensive.

DESCRIPTION OF THE INVENTION

It is an object of the present invention to provide a new and improved technique for varying the operating range for the comminution of concrements whereby on one hand the ignition in the submerged arc device will not vary as far as ignition voltage is concerned while the capacitance is likewise kept constant but still, the amount of energy used can be reduced.

In accordance with the preferred embodiment of the present invention it is suggested to provide a set of different electrode assemblies to the user and to connect an ohmic resistance directly in series with these electrodes. The ohmic resistance is included as a component in the electrode structure as far as mounting is concerned, and in the case of coaxial feed system it is the inner conductor which contains the resistor or even constitutes by itself the ohmic resistor. The resistors are preferably constructed of stainless steel and the resistance values differ from each other in a range from 0.1 to 1 ohm. Any heat is conducted out of the system in the normal fashion.

It can thus be seen that it is essential for the invention to provide a supplemental ohmic resistance structure between the shock wave energy source, e.g. the capacitor and the arc discharge gap. This ohmic load is selectively interconnected, and exchanged for different comminution tasks. These ohmic resistors will convert into heat some of the energy that is not needed for any specific instance of arc generation. It is essential that this series resistor is much lower than the resistance of the underwater gap between the electrodes so that it does not interfere with the arc ignition. The underwater gap has typically a resistance in the kiloohm range. On the other hand, the ohmic resistance is comparable with the resistance of a fully developed plasma channel between these electrodes. This resistance has a conductivity is typically several ohms. For this reason, the ignition voltage has to remain high and constant. Only after a low impedance plasma channel has developed in the underwater discharge gap and after the capacitor actually begins to discharge, the low ohmic impedance will show its effect. As stated, the resistor will generally be above about 1.10 ohm but not more than about 1 ohm so that the resistor will not interfere with the breakdown mechanism mentioned above and during which operation the gap resistance is in the kiloohm range.

The electrodes are usually mounted in a particular structure which, as a whole, is exchangeable for ease of refurnishing or the like, and it is of advantage to provide the ohmic resistor as an inner conductor or part of the inner conductor in a coaxial conductor system being a part of an exchangeable electrode structure. The inner conductor is normally made of a highly conductive material and is normally comprised, e.g. of silver plated brass, just as is the outer conductor. The resistance now is included in a series circuit connection, particularly int he path of the inner conductor, in that at least a portion of the inner conductor is made to be of a fairly poorly conducting medium.

The principle of variability concerning the ohmic resistance in the circuit can be extended to include the electrode tips themselves, e.g. one or the other of the electrodes or both can be made of a fairly poor electrical conductor.

The electric power dissipated as heat in such a resistor when between 0.1 and 1 ohm, is in the order of 30W maximum for the lower ohm value. It was found that natural thermal conduction suffices for removing the heat. It is preferred to use coaxial transmission. In this case the inner conductor portion may be exchangeable within a given electrode-plus-conductor assembly or one used fixed assemblies of that kind with the inner conductors having different resistances. Still alternatively, a resistance change can be made to take place, e.g. through temperature control or pressure/tension application, though switching actions should be avoided.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a circuit 2 which shows connectors 3 to be connected to a suitable power supply source. The circuit further includes a capacitor 4 which may be charged through a high ohmic structure, not shown, and that may be included in the circuit to which circuit 2 is connected by means of the connectors 3 and being part of the charge circuit. Reference numeral 8 refers to a spark gap composed of and defined by electrodes 8*a* and 8*b*, placed in a certain distance from each other. Detailed configurations will be shown and explained more fully below.

One of these electrodes (8*b*) is connected directly to the grounded side of the capacitor 4, and it is usually that side which is grounded. The other electrode (8*a*) is connected to a resistor 10 which is part of the invention and is incorporated in the circuit and device in a manner to be described more fully below. A gap 6 is connected in series with the resistor 10, which, in this case, is a switching spark gap and which will be ignited in case the voltage on the capacitor exceeds a certain limit. In lieu of this particular spark gap 6, one could provide a switch that is manually or electronically operated or the like. Structure is provided in the circuit for interrupting or permitting current flow by providing a very low ohmic connection.

Figure 1:
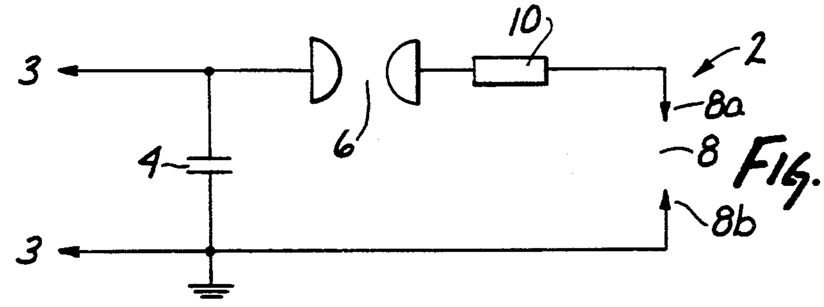
FIG. 1 shows a circuit in accordance with the preferred embodiment of the invention with integrated ohmic resistors.
Figure 2:
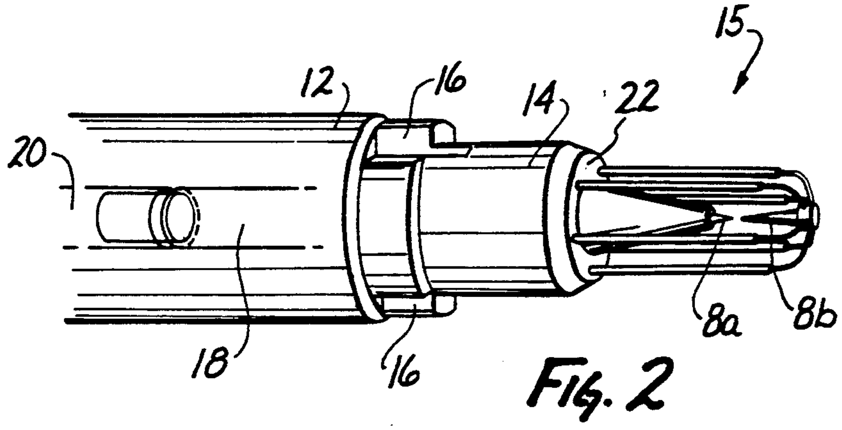
FIG. 2 is an example for a typical exchangeable electrode structure as inserted and in which the invention is incorporated and used in the specific way.
Figure 3:
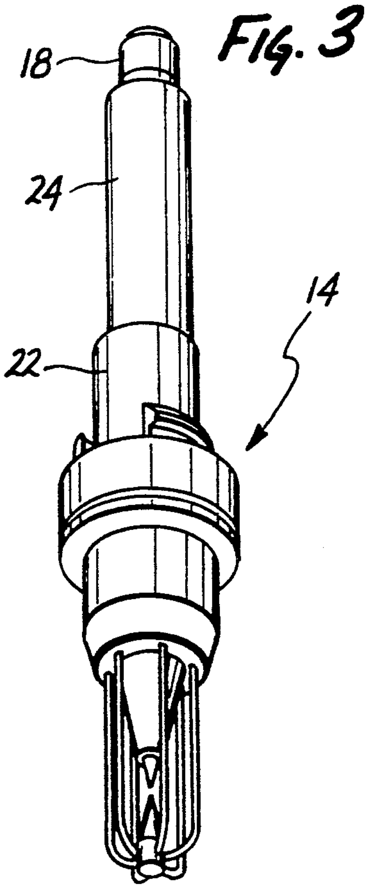
FIG. 3 shows the electrode assembly itself as used in the device shown in FIG. 2.

The electrode structure is shown in greater detail in FIG. 2 and 3. It includes a sleeve serving as a holder 12 into which the electrode arrangement 14 is plugged. The electrode assembly includes the outer electrode cage element 15 for holding electrode 8*b*, and the inner electrode 8*a*, which is continued in a tip element, the front of which faces the tip of the electrode 8*b*. The various applications and patents referred to above show details of this particular structure which, as far as the electrode proper is concerned, is directly incorporated and includes in particular the cage element 15 on which the tip element is mounted for the grounded electrode 8*b*.

The cage 15 is connected to and extends from the outer conductor 22, and the inner electrode 8*a* is connected in a series with the inner conductor 18. The inner conductor 18 is separated from the outer conductor 22 by means of an insulation 24. The element shown in FIG. 3 is the one that is been plugged-in into the sleeve arrangement 12.

Figure 4:
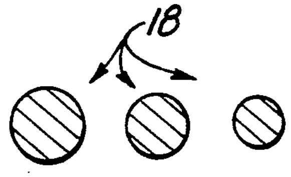
FIGS. 4 and 5 show possible variations in the inner conductor to obtain the electrode set variability.
Figure 5:
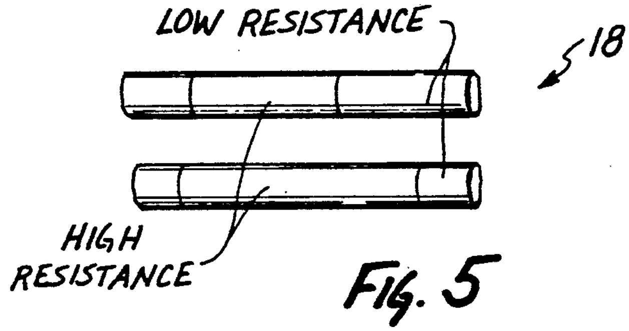

As far as the invention is concerned, a plurality of these devices shown in FIG. 3 is suggested. It is essential that as far as overall geometry is concerned, the overall positioning of all these electrodes and their respective assembly are the same. They differ in the effective (numerical) electrical ohmic resistance of the inner conductor 18. That inner conductor 18 is different in the different configurations in that the cross section (FIG. 4) and/or material composition (FIG. 5) and/or effective length and/or the length of a portion being reduced in cross-section, to obtain the requisite variety of resistances.

Typically, a resistance of not lower than 100 millohms is needed while the upper limit for practical purposes is in the order of 1 ohm. The variability covers, therefore, a range that extends over, roughly one order of magnitude. In the case of a specific lithotripter whenever a specific task requires a particular shock wave range and particular impedance and resistance within the electrode assembly, one can simply exchange the electrode structure for the one that is specifically adapted to the task at hand in terms of internal resistance in series with the submerged spark gap. The adaptation merely requires a proper selection of the ohmic resistances within the spark gap circuit.

The invention is not limited to the embodiments described above but all changes and modifications thereof, not constituting departures from the spirit and scope of the invention, are intended to be included.

I claim:

1. A kit adapted to be used in an arrangement for the comminution of concrements of various kinds in the body of a living being, the arrangement including an underwater arc gap established by an electrode assembly and an electrical energizing circuit adapted for connection to that electrode assembly, comprising:

a plurality of electrode assemblies from which one is selected for connection to the electrical energizing circuit, to serve as said electrode assembly when so connected to the energizing circuit, said electrode assemblies being basically similarly configured, and each having an ohmic resistor connected directly in series with one electrode, of the electrode assembly when connected to the energizing circuit;

the respective resistance values for the resistors in the electrode assemblies being different so that different amounts of energy will be dissipated in the gap between the electrodes resulting in different shockwave intensities on discharge in the respective gap for different ones from said plurality of assemblies as selected from the kit and when connected to the energizing circuit.

2. A kit as in claim 1, wherein each of the electrode assemblies includes an inner conductor and an outer conductor together in each instance constituting a concentric arrangement and wherein in each instance the inner conductor is configured as said ohmic resistor.

3. A kit as in claim 1, wherein the ohmic resistor is stainless steel.

4. A kit as in claim 1, wherein the lowest ohmic resistance value of the ohmic resistor in the assembly is about 100 mohm and the highest is in the order of 1 ohm.

* * * * *